United States Patent
Jennissen

(12) 
(10) Patent No.: US 7,255,872 B2
(45) Date of Patent: Aug. 14, 2007

(54) METHOD FOR IMMOBILIZATION OF MEDIATOR MOLECULES ON METALLIC AND CERAMIC IMPLANT MATERIALS

(75) Inventor: Herbert Peter Jennissen, Essen (DE)

(73) Assignee: Morphoplant GmbH, Bochum (DE)

( * ) Notice: Subject to any disclaimer, the term of this patent is extended or adjusted under 35 U.S.C. 154(b) by 332 days.

(21) Appl. No.: 10/646,913

(22) Filed: Aug. 21, 2003

(65) Prior Publication Data

US 2004/0074568 A1    Apr. 22, 2004

Related U.S. Application Data

(62) Division of application No. 09/554,972, filed as application No. PCT/DE98/03463 on Nov. 24, 1998, now Pat. No. 6,635,269.

(30) Foreign Application Priority Data

Nov. 24, 1997  (DE) ................. 197 52 032

(51) Int. Cl.
*A61F 2/00* (2006.01)
*C12N 11/14* (2006.01)
*A61K 38/00* (2006.01)
*C07K 17/14* (2006.01)

(52) U.S. Cl. .............. 424/423; 435/176; 514/2; 530/402; 530/811

(58) Field of Classification Search ............... None
See application file for complete search history.

(56) References Cited

U.S. PATENT DOCUMENTS

| | | | |
|---|---|---|---|
| 2,375,210 A | 6/1945 | Batcheller | |
| 4,002,602 A * | 1/1977 | Goldstein | 530/324 |
| 4,190,647 A * | 2/1980 | Goldstein et al. | 514/17 |
| 4,371,612 A * | 2/1983 | Matsumoto et al. | 435/44 |
| 5,306,307 A | 4/1994 | Senter et al. | |
| 5,330,911 A | 7/1994 | Hubbell et al. | |
| 5,837,235 A | 11/1998 | Mueller et al. | |
| 6,635,269 B1 | 10/2003 | Jennissen | |

FOREIGN PATENT DOCUMENTS

| | | |
|---|---|---|
| GB | 387806 | 2/1933 |
| GB | 593287 | 10/1947 |
| WO | WO 90/09798 | 9/1990 |
| WO | WO 92/00047 | 1/1992 |

OTHER PUBLICATIONS

International Search Report for Application PCT/DE98/03463.

* cited by examiner

*Primary Examiner*—David M. Naff
(74) *Attorney, Agent, or Firm*—Foley & Lardner LLP

(57) ABSTRACT

A mediator molecule is immobilized on the surface of a metallic or ceramic implant material. An anchor molecule (e.g., dialdehyde or cyanogen bromide) having a functional group that covalently binds the mediator molecule is covalently bound to the surface, and the mediator molecule is coupled to the functional group of the anchor molecule. The implant material may comprise titanium, titanium alloy, aluminium or stainless steel or hydroxylapatite. Oxide units on the implant material surface can be increased preferably by treating with hot chromic-sulphuric acid for 0.5 to 3 hours at a temperature between 100 to 250° C. prior to binding the anchor molecule. Also, prior to binding the anchor molecule, the surface of the implant material can be activated by reacting with a silane derivative. Mediator molecules include BMP protein, ubiquitin and antibiotics, and the implant material may be an artificial joint or coronary vessel support such as a stent.

9 Claims, 2 Drawing Sheets

METHOD FOR IMMOBILIZATION OF MEDIATOR MOLECULES ON METALLIC AND CERAMIC IMPLANT MATERIALS

This application is a divisional application of previously allowed U.S. application with the Ser. No. 09/554,972, which was filed May 23, 2000 now U.S. Pat. No. 6,635,269 B1, which is a national phase application of international application PCT/DE98/03463, filed Nov. 24, 1998.

BACKGROUND OF THE INVENTION

1. Field of the Invention

The present invention relates to a method for the immobilization of mediator molecules on surfaces of metallic or ceramic materials which are used for implants such as artificial joints or also microimplants, for example so-called stents, as well as implants produced according to the method.

2. Description of the Related Art

The implantation of artificial joints or bones has gained increasing importance in recent years, for example in the treatment of joint dysplasias or joint dislocations or in sicknesses resulting from joint attrition as a result of improper joint positioning. The function of the implants and the materials used for their production, which, in addition to metals such as titanium or metal alloys, can also include ceramics or synthetic materials such as teflon, have been continually improved, so that following a successful healing process, implants exhibit lifetimes of 10 years in 90-95% of all cases. Yet despite this progress and these improved operational methods, an implantation still remains a difficult and strenuous operation, particularly since it is associated with a long process of healing-in of the implants, often including month-long stays in clinics and health resorts, including rehabilitation measures. In addition to the pain, the length of the treatment period and the separation from familiar surroundings represent heavy stresses for the affected patients. In addition, the long healing process incurs high personal and treatment costs due to the required intensive care.

The understanding of the molecular-lever processes required for a successful growing-in of an implant has markedly increased in recent years. Structural compatibility and surface compatibility are crucial for the tissue tolerability of an implant. Biocompatibility in a narrower sense depends only on the surface. Proteins play a crucial role at all levels of integration. These form an initially adsorbed protein layer as early as during the implantation operation and thus, as explained below, since the first cells will later colonize on this layer, determine the further progression of the healing-in of the implant.

In the molecular interaction between implant, also referred to as biomaterial, and tissue, a multitude of reactions take place which seem to be strictly hierarchically ordered. The adsorption of proteins on the surface of the biomaterial is the first biological reaction which takes place. In the resulting protein layer, single protein molecules are for example either transformed by conformational changes to signal substances which are presented on the surface, or protein fragments functioning as signal substances are released by catalytic (proteolytic) reactions. Triggered by the signal substances, cellular colonization takes place in the next phase, and can include a multitude of cells such as leucocytes, macrophages, immunocytes and finally also tissue cells (fibroblasts, fibrocytes, osteoblasts, osteocytes). In this phase other signal substances, so-called mediators such as for example cytokines, chemokines, morphogens, tissue hormones and true hormones play a decisive role. In the case of biocompatibility, there is a final integration of the implant into the entire organism, and one ideally obtains a permanent implant.

In light of work performed in recent years at the molecular level of osteogenesis, chemical signal substances, the so-called "bone morphogenic proteins" (BMP-1-BMP-13), which influence bone growth, have gained increasing importance. BMPs (in particular BMP-2 and BMP-4, BMP-5, BMP-6, BMP-7) are osteoinductive proteins which stimulate the formation of new bones and bone healing by effecting the proliferation and the differentiation of precursor cells to osteoblasts. Furthermore they promote the formation of hormone receptors, bone-specific substances such as collagen type 1, osteocalcin, osteopontin and finally mineralization. Here, the BMP-molecules regulate the three key reactions chemotaxis, mitosis and differentiation of the respective precursor cells. In addition, the BMPs play an important role in embryogenesis, organogenesis of bone and of other tissue, wherein osteoblasts, chondroblasts, myoblasts and vascular smooth muscle cells (proliferation inhibition by BMP-2) are known as target cells.

SUMMARY OF THE INVENTION

A particular aim in the immobilization method according to the invention is a degree of stimulation (that is, surface concentration of the immobilized protein) which allows a multivalent interaction between surface and cell and enables the effective control of bone and tissue formation.

To date, 13 BMPs including multiple isoforms are known. With the exception of BMP-1, the BMPs belong to the "transforming growth factor beta" (TGF-β) superfamily, for which specific receptors on the surface of the corresponding cells have been found. As the successful use of recombinant human BMP-2 and/or BMP-7 in experiments on defective healing processes in rats, dogs, rabbits and monkeys has shown, no species-specificity seems to exist. Previous attempts to exploit the bone formation-triggering characteristics of the BMPs for implantation purposes, in which BMP-2 and/or BMP-7 were noncovalently applied to metallic or ceramic biomaterials, have however been largely unsuccessful.

The goal of the present invention is to produce improved biomaterials for use as implants.

DETAILED DESCRIPTION OF THE INVENTION

Figure 1:
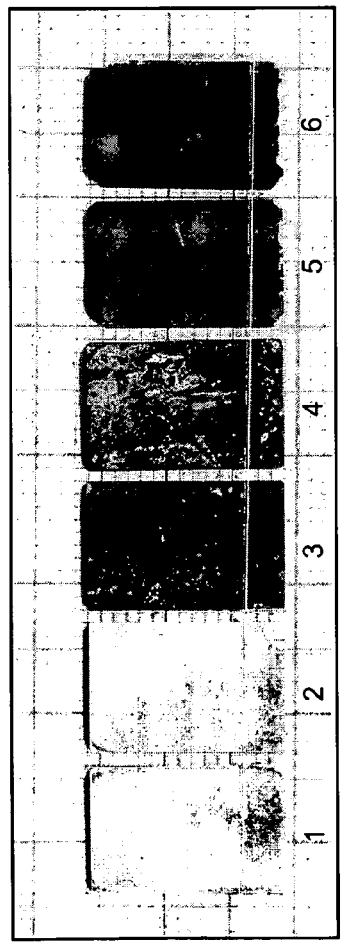
FIG. 1 is a photograph showing various substrates with oxidized $TiO_2$ flakes.

According to the invention this goal is achieved by the provision of a method for the immobilization of mediator molecules on metallic and ceramic materials. In the method according to the invention, in a first step a chemical compound is covalently bound to the surface of the implant material as an anchor molecule, wherein this chemical compound has a functional group which can either be bound itself as a spacer molecule or to another compound serving as a spacer molecule. In a second step a mediator molecule such as a bone growth factor can be immobilized on the implant material via functional groups, for example free amino groups or carboxylate groups by means of a covalent bond. In this way it is possible to form a chemotactic and/or biologically active implant surface (a so-called juxtacrine surface), which leads to the colonization, proliferation and differentiation of bone cells.

The method according to the invention for the immobilization of the mediator molecules is distinguished by the fact that the implant material used is composed of metallic materials such as pure titanium or metallic titanium alloys such as chrome/nickel/aluminium/vanadium/cobalt-alloys (for example TiAlV4, TiAlFe2.5), stainless steels (for example V2A, V4A, chrome-nickel 316L) or ceramic materials such as hydroxylapatite, aluminium oxide or of a combination, in which for example metallic material is coated with ceramic material. Synthetic polymer materials are also suited for use as the implant material.

Further subject matter of the invention is the therapeutic prevention or alleviation of the late complication restenosis elicited by a proliferation of smooth vessel muscle cells by coating a coronary vessel support (so-called coronary stent, length approximately 10 mm) with the help of a biomolecule or a mediator, for example BMP-2, in order to promote healing-in and tolerability.

According to the invention the mediator molecules can be biomolecules which are advantageous for the biocompatibility of the implant in that they hinder a possible rejection of the implant and/or promote growing-in of the implant.

Preferred mediator molecules which can be used in the present method are bone growth-promoting proteins from the class of bone growth factors "bone morphogenic proteins" or also ubiquitin. It can be advantageous for the immobilization to use one protein of this class alone, in combination with other members of this class or also together with biomolecules such as proteins of other classes or low molecular weight hormones or also antibiotics to improve immunoresistance. Here, these molecules can also be immobilized on the surface via bonds which are cleavable in the biological environment.

According to the invention the surface of implant material is chemically activated, wherein the activation takes place via a silane derivative such as for example γ-aminopropyl-triethoxysilane or a trimethylmethoxy- or trimethylchlorosilane derivative or 3-glycidoxypropyltrimethoxysilane and the reaction is performed not only in an aqueous but also in an organic solvent. In a second step a spacer molecule serving as a spacer can be covalently coupled to the surface activated in this way. A dialdehyde such as glutaric dialdehyde, an isothiocyanate derivative or a triazine derivative can for example serve as the spacer. A dicarboxylic acid or a corresponding derivative such as succinic acid can be used as the spacer molecule. Following possible activation of the coupling group present in the spacer molecule, for example a carbonyl functionality, by way of a common method for this purpose, the bone growth-promoting protein is bound to the implant material via amino groups accessible on its surface.

According to the invention it is also possible to use an aryl amine as a spacer molecule. This can for example be obtained by reaction of the implant material activated by a silane compound with a benzoic acid chloride substituted with nitro groups such as for example p-nitrobenzoylchloride followed by reduction of the nitro group. In this case covalent linking of the mediator protein takes place via three carboxyl groups which can be activated according to standard procedures for this purpose.

The present method further includes coupling of the mediator molecule via anchor molecules only, without prior activation of the implant surface by silane as described above by way of example, wherein cyanogen bromide can for example be used for this purpose. In this case the covalent immobilization of the mediator molecule can take place via three amino groups of the protein.

The method according to the invention includes the coupling of a bone growth factor to the surface of the implant via spacer molecules, the covalent bonds of which are not cleaved under physiological conditions. As an advantageous development, a bone growth factor is coupled to the surface of the implant via spacer molecules, the covalent bonds of which are cleavable under physiological conditions for a limited release of the mediator protein. Alternatively it is also possible to couple the bone growth factors without the help of the spacer molecule, for example by way of the carbodiimide method, to the activated surface of the implant.

According to another further development of the method, two or more spacer molecules are used for the immobilization of at least one bone growth factor.

The loading density of the mediator protein immobilized on the implant material according to the method of the invention is generally 0.03 to 2.6 µg/cm$^2$ (for example 1-100 pmol/cm$^2$ BMP-2). In this loading range, a multivalent interaction between a cell (for example 10 µm diameter) and the BMP-molecules on a biologicalized surface can be achieved, since approximately $10^6$-$10^8$ immobilized protein molecules are located in the adhesion site.

The inventors have performed extensive experiments to elucidate the mechanism of the binding of the protein molecules to the surface. In the course of this, they found that with metallic surfaces such as for example with titanium the binding takes place via covalent bonds via the titanium dioxide molecules formed on the metal surface, which are preferably transformed into hydroxyl groups by treatment with dilute nitric acid.

In contrast to the methods known in the prior art, in which biomolecules are for example deposited onto polymer surfaces or inorganic bone materials and remain on the surface of the substrate only via affinity interactions with the polymer molecules, the inventors have been successful here in covalently anchoring the biomolecules to the surface and, in this way, providing them for a longer time on the surface of the implant.

Further investigations by the inventor have shown that the anchoring of the mediator molecules on the surface can be qualitatively and quantitatively improved by increasing the number of the accessible metallic oxide units on the surface. It was found by the inventors that the number of oxide groups can surprisingly be increased by treating the surface of the metal with hot, preferably sediment-free chromic-sulfuric acid. In contrast to the expectation that the metal dissolves under these conditions, a relatively uniform oxide layer is generated on the surface of the metal by the use of this acid. The method is so mild that even coronary vessel supports, so-called stents (which can for example be fashioned from stainless steel or titanium) can be coated without destroying the thin sensitive meshing (50-150 µm diameter). In this way the oxide layer can reach a thickness of 10 µm up to 100 µm and can be relatively "smoothly" constructed without pits or holes. Pure titanium or titanium alloys (for example TiAlV4, TiAlFe2.5), aluminium or stainless steel (for example V2A, V4A, chrome nickel 316L) can be used as the metal for the implant. A common commercial chromic-sulfuric acid of 92% by weight $H_2SO_4$, 1.3% by weight $CrO_3$ and with a density of 1.8 g/cm$^3$ as for example available from the company Merck is preferably used to achieve a thin smooth layer of metal oxide. In order to achieve this, the metal substrate is placed in the chromic-sulfuric acid and is treated over a time span of 1 up to 3 hours at 100 to 250° C., preferably 30 min at 240° C., is subsequently carefully rinsed with water, is boiled in water or in a solution of 1-4 mM EDTA (ethylenediaminetetraacetate), preferably 4 mM EDTA for 30 min, in order to remove the chrome ions remaining on the surface, and is then dried.

If a thicker metal oxide layer and/or an oxide layer with small micro- and nanopores is to be provided on the metal surface, the chromic-sulfuric acid described above is diluted with water to a density of 1.5 to 1.6 g/cm$^3$. In a subsequent treatment of the surface of the metal implant as described above with the acid diluted in this way, a "rough" surface layer with pits and pores is formed, so that the surface available for loading with mediator molecules is increased. It is therefore possible to apply a multitude of different oxide layers with different characteristics to metal surfaces with high adhesion by tuning to various densities of chromic-sulfuric acid. The invention is therefore also directed to such a method for forming a thermodynamically unified metal oxide layer (no contact angle hysteresis) on the implant material by means of hot chromic-sulfuric acid.

The metal oxide layer on the implant material made of the materials cited above can then be activated via treatment with dilute nitric acid (approximately 5% by weight) and subsequent coupling of a silane derivative, optionally additionally of a spacer molecule, as described above. The mediator molecules can then be anchored via the molecules of the silane derivative or of the spacer via coupling methods such as for example by way of carbonyldiimidazole on the implant surface.

In order to exclude the nonspecific adsorption of the mediator molecules, which can be up to 30% of the adsorbed mediator molecules on the metal surface, it is further preferred in the scope of the present invention to first couple an adsorption-preventing layer of spacer molecules such as for example agarose to the surface of the implant on which the metal oxide layer is provided, to which adsorption-preventing layer the mediator molecules can then be coupled. A prevention of nonspecific adsorption can make sense in order to for example preclude a blocking of BMP-receptors as a result of conformational changes of the BMP-proteins following nonspecific adsorption to the surface. The invention is therefore also directed to such a method for the formation of a nonspecific binding-preventing coating on the metal oxide layer and subsequent coupling of the mediator molecules. The use of a coating of agarose for this purpose is preferred.

A ceramic material such as for example hydroxylapatite can be used as the implant material. Here, the hydroxylapatite should first be activated by treatment with aminoalkylsilane and then reacted with a coupling agent such as carbodiimidazole. In the next step a coupling of the mediator molecules such as BMP or ubiquitin to the surface can take place. When using hydroxylapatite, the use of spacer molecules is not necessarily required.

In the case that the mediator molecules used are not easily soluble under the coupling conditions, the solubility can be increased by addition of surfactants/detergents and the reaction can be performed. In this way, difficultly soluble bone growth factors and other mediators can be kept in solution at pH-values>6 without losing biological activity by ionic and nonionic detergents in the concentration range of 0.05-10%, preferably 1-5% by weight, in particular 0.066% SDS at pH-values>6, in particular pH 8-10 for the covalent coupling method at alkaline pH.

The influence of materials modified by the method of the invention on bone cells or on osteoblast cell lines (MC3T3-E1) were studied in cell culture systems, wherein the modified materials were presented in flake form for this purpose. It was observed that, following application of the cells, confluent cell lawns formed and functional changes by BMP-2 (for example synthesis of alkaline phosphatase) on the materials took place.

The present invention will now be further explained with the help of the following examples. The experiments were performed with highly pure human BMP2 as well as ubiquitin produced in house by genetic engineering or commercially obtained (company: Biochrom KG/Seromed, Berlin).

EXAMPLE 1

Immobilization of BMP on Powdered Titanium with Spacer a) Production of a Implant Surface Capable of Reaction 0.5 g titanium powder (particle diameter 50-100 µm) are added to 9 ml distilled water and, depending on the degree of substitution, 0.2-2 ml 10% (v/v) γ-aminopropyltriethylethoxysilane are added and the pH of this reaction batch is adjusted to a value between 3 and 4 by addition of 6 N HCl while stirring. After regulation of pH, the reaction solution is incubated in a water bath for 2 h at 75° C. Subsequently the activated metal is separated by vacuum filtration, is washed with approximately 10 ml distilled water and is dried in a drying cabinet at 115° C.

b) Activation of the Implant Surface and Insertion of a Spacer Molecule 0.5 g of the metal powder derivatized with the aminoalkylsilane is added to 12.5 ml 2.5% glutaraldehyde in 50 mM $NaH_2PO_4$, pH 7.0. The reaction is carried out to conversion or until a change of color is observed. The reaction product is subsequently separated over a filter and is washed with copious amounts of distilled water.

c) Immobilization of Protein

To the washed reaction product with glutaraldehyde is added BMP in an amount of 0.1-3.0 mg/g titanium powder, 0.066% sodium dodecyl sulfate (SDS) at neutral pH followed by reaction overnight at 4° C.

EXAMPLE 2

Immobilization of BMP on Powdered Titanium Without a Spacer a) Production of an Implant Surface Capable of Reaction The production of an implant surface capable of reaction took place in the same way as in Example 1.

b) Activation of the Surface of the Implant 1.0 g of the metal derivatized with the aminoalkylsilane derivative is added to 50 ml 0.03 M $H_3PO_4$ with a pH adjusted to 4.0. To this were added 100-200 mg of a water soluble carbodiimide, for example 1-cyclohexyl-3-(2-morpholinoethyl) carbodiimide-methoxy-p-toluene sulfonate.

c) Immobilization of the Protein

BMP is added directly to the activated titanium powder mentioned above in an amount of 0.1-3.0 mg/g titanium powder and is incubated overnight at 4° C.

EXAMPLE 3

Immobilization of BMP on Flake Shapes Titanium with Spacer a) Production of an Implant Surface Capable of Reaction The activation of the implant surface took place in the same way as in Example 1. Instead of titanium powder the same amount of titanium flakes was simply used.

b) Activation of the Implant Surface and Insertion of a Spacer Molecule

The metal flake activated with the aminoalkylsilane derivative is added to 12.5 ml 2.5% glutaraldehyde in 50 mM $NaH_2PO_4$, pH 7.0. Reaction is carried out until a change of color is observed. Subsequently the reaction product is separated over filter and is washed with copious amounts of distilled water.

c) Immobilization of the Protein

BMP in an amount of 0.1-3.0 mg/g titanium flakes is added to the washed reaction product at neutral pH and is incubated overnight at 4° C.

EXAMPLE 4

Immobilization of BMP on Flaked Titanium Without Spacer a) Production of an Implant Surface Capable of Reaction The activation of the implant surface took place in the same way as in Example 1. Instead of titanium powder the same amount of titanium flakes was simply used.

b) Activation of the Implant Surface

The metal flakes derivatized with the aminoalkylsilane are added to 50 ml 0.03 M $H_3PO_4$ with a pH adjusted to 4.0. To this were added 100-200 mg of a water soluble carbodiimide for example 1-cyclohexyl-3-(2-morpholinoethlyl)-carbodiimide-methoxy-p-toluene sulfonate).

c) Immobilization of the Protein

BMP was added directly to the coupling batch mentioned above in an amount of 0.3-3.0 mg/g titanium flakes and is incubated overnight at 4° C.

EXAMPLE 5

Slow-Release-Immobilization of BMP on Flaked Titanium Without Spacer a) Activation of the Implant Surface 1 titanium flake (0.5×1.0 cm) with a thickness of 0.1 to 0.5 mm is added to 25 ml distilled water. The pH is adjusted to 10-11 and 1 g CNBr is added while maintaining the pH at 10-11 and while maintaining the temperature at 15-20° C. When the pH-value no longer changes, the reaction is completed and the metal flake is washed with 100 ml $H_2O$.

b) Immobilization of the Protein

BMP is added to the metal plate activated with CNBr in an amount of 0.1-3.0 mg/g flake in 0.066% SDS and is incubated overnight at pH 9.0 and 4° C. The coupling reaction can also be carried out at pH 7.0. The flake is thoroughly washed after the coupling. The covalent bond between the metal flake and BMP hydrolyzes with a half-life of about 1-4 weeks so that soluble BMP is released.

EXAMPLE 6

Immobilization of BMP on Flaked Hydroxylapatite Without Spacer a) Production of an Implant Surface Capable of Reaction Hydroxylapatite is reacted overnight in 10% solution of aminopropyltriethylethoxysilane in toluene under reflux conditions. After this the hydroxylapatite is washed with toluene and is dried.

b) Activation of the Implant Surface 1.0 g of the apatite made capable of reaction with the aminoalkylsilane derivative is added to 50 ml 0.03 M $H_3PO_4$ with a pH adjusted to 4.0. To this are added 100-200 mg of a water soluble carbodiimide, for example 1-cyclohexyl-3-(2-morpholinoethlyl)-carbodiimide-methoxy-p-toluene sulfonate.

c) Immobilization of the Protein

BMP is added directly to the coupling batch mentioned above in an amount of 1-10 mg/g of hydroxylapatite and is incubated overnight at 4° C.

EXAMPLE 7

Immobilization of BMP on Flaked Hydroxylapatite with Spacer a) Production of an Implant Surface Capable of Reaction Hydroxylapatite is reacted overnight in a 10% solution of γ-aminopropyltriethylethoxysilane in dry toluene under reflux conditions. After this hydroxylapatite is washed with toluene and is dried.

b) Activation of the Implant Surface and Insertion of a Spacer Molecule 0.5 g of the apatite made capable of reaction with the aminoalkylsilane derivative is added to 12,5 ml 2.5% glutaraldehyde in 50 mM $NaH_2PO_4$, pH 7.0. The reaction is carried out to conversion or until a change in color is observed. Subsequently the reaction product is separated over a filter is washed with copious amounts of distilled water.

c) Immobilization of the Protein

BMP is added directly to the coupling batch mentioned above in an amount of 1-10 mg/g hydroxylapatite and is incubated overnight at pH 7.0 at 4° C.

In place of the methods given in the production examples under 2a, 4a and 6a, an implant surface capable of reaction can also be provided in the following way. For this, 0.5 g of metal powder, 1 metal flake or 1 g apatite is allowed to react overnight in a 2% solution of 3-glycidoxypropyltrimethoxysilane (GPS) in dry toluene under reflux conditions. After this the respective sample material is washed with toluene and is dried under vacuum. 15 ml the acetic acid/$H_2O$ (90:10) containing 0.83 g sodium periodate were added to the above amounts of GPS to form a primary hydroxy derivative capable of reaction from the epoxy derivative. The batch is mixed for 2 h at room temperature and incubated. The liquid phase is then removed and is washed with water, acetone and diethylether (20 ml, respectively). It can then be incorporated into one of the above mentioned activation reactions.

Instead of the methods given in the production examples under 2b, 4b and 6b, the activation of the implant surface can also take place in the following way. For this 0.5 g of the metal powder (2a) derivatized with the aminoalkylsilane or a metal flake derivatized with aminoalkylsilane (4a) or 1.0 g of the apatite (6a) made capable of reaction with the aminoalkylsilane derivative are washed with 50 ml water-free acetone (<0.3%). Then, 10 ml of a solution of 3% carbonyldiimidazole/acetone are added to the silane-derivatized material and are incubated 30 min at room temperature. Washing with 20 ml acetone follows, and then the coupling with the protein BMP can take place.

EXAMPLE 8

Checking of the Biological Activity of Immobilized BMP in Cell Culture According to Bingmann In this test the biological efficacy of BMP in vitro on primary cultures of bone explants (guinea-pig calvaria cells) is investigated: adhesion number, growth, proliferation, functional changes in the hormone stimulability and in the spreading of reinduced ionic signals (for example calcium ions and $H^+$-ions). The metal samples (flakes) are coated with BMP in such a way that one half of the flake is biologicalized and the other half serves as a control. Initial results prove that the flakes coated with BMP effect a marked functional change of the bone cells.

EXAMPLE 9

Coding of Titanium Powder with Protein a) Hydroxylation with Nitric Acid 2 g titanium powder (atomized<60 μm) is stirred for 2 h at 80° C. in 5% HNO3 under reflux. Afterwards the powder is separated over a frit and is washed with 500 ml water (pH=6-7). The powder is further washed with 30 ml dry ethanol.

b) Silanization with 3-Aminopropyltriethoxysilane (APS)

1 g hydroxylated titanium powder is suspended in in 45 ml dry toluene and is treated with 5 ml APS under nitrogen as a protective gas (working in an atmosbag). The suspension is boiled for 4 h under reflux. Separation over a frit and washing with 200 ml toluene and 100 ml ethanol follows. The substance is dried with acetone.

c) Activation of the Silane Powder with Carbonyldiimidazole (CDI)

750 mg of CDI are dissolved in 15 ml of dry acetone and are treated with 300 mg of the product of 2). The mixture is stirred at room temperature for 3 h and then separated over a frit. Further washing with 50 ml acetone and 50 ml water follows.

d2) Coupling with 125I-Ubiquitin

Ubiquitin is 125-iodinated with the help of Chloramine T according to a known method. 100 mg of the silane powder of 3) are suspended in 1 ml of a buffer solution of 50 mM Na-phosphate buffer, pH 10.0, in which 1 mg/ml 125I-ubiquitin of a specific radioactivity of 5000-20000 cpm/μg is dissolved. The ubiquitin concentration can be between 0.01 and 1.0 mg/ml. The mixture is rotation-stirred (German: am Rad gerührt) 2 h at room temperature and is then stirred overnight. The supernatant is pipetted off. Washing three times with 1 ml buffer follows. Washing four times with a solution of 0.1 M NaOH, 1% sodium dodecyl sulfate (SDS) and two more times with buffer and two times with water follows. The titanium powder coated with 125I-ubiquitin is mixed in a small Eppendorf tube with 1 ml acetone. The supernatant is pipetted off and the powder is dried overnight under oil-pump vacuum.

Controls are carried out with the activated and/or nonactivated product of 2) (see Table 1).

d2) Coupling with 125I-BMP-2

The coupling of BMP-2 to ubiquitin takes place analogously, with the difference that 50 mM Na-borate, 0.066% SDS at pH 10 is used as the buffer. The concentration of BMP-2 was between 0.01-1 mg/ml.

TABLE 1

| Protein coupling to titanium powder by way of example of the protein 125I-ubiquitin | |
|---|---|
| | Immobilized 125I-ubiquitin on titanium powder (2400 cm2/g) μg/cm2 |
| A. Adsorption: | |
| Ubiquitin on pure titanium powder | 0.638 |
| Ubiquitin on APS-modified titanium powder | 0.417 |
| after NaOH/SDS treatment | 0.107 |
| B. Covalent coupling of ubiquitin* | |
| Experiment method 1: | |
| control | 0.107 |
| covalent coupling | 0.122 |
| Experiment method 2: | |
| control | 0.035 |
| covalent coupling | 0.094 |

*Definition of the covalently bound protein: the amount of protein which is measured following washing with 0.1 M NaOH/1% SDS (see method).

EXAMPLE 10

Coating of Titanium Flakes with an Oxide Layer to Increase the Protein Binding Capacity The oxidation of the titanium flakes (each about 0.5×1 cm) is carried out in boiling chromic-sulfuric acid at a temperature of 190-200° C. for 1.5 h. The flakes, having become grey by the oxidation, are thoroughly rinsed with water. After this the flakes are boiled in water for 30 min. The flakes are dried at room temperature (RT) in the air (see FIGS. 1 and 2—the flakes 1 and 2 shown in FIG. 1 are untreated, the flakes 3 and 4 are treated with chromic-sulfuric acid of density 1.8 g/cm$^3$, the flakes 5 and 6 are treated with chromic-sulfuric acid of density 1.6 g/cm$^3$). An EDX-analysis (Energy Dispersive Analysis of X-rays) under scanning electron microscope control of the new layer yielded up to 90% TiO2.

As shown in FIG. 1, the oxidized TiO2-flakes are clearly more darkly colored and have completely lost their metallic shine.

Figure 2:
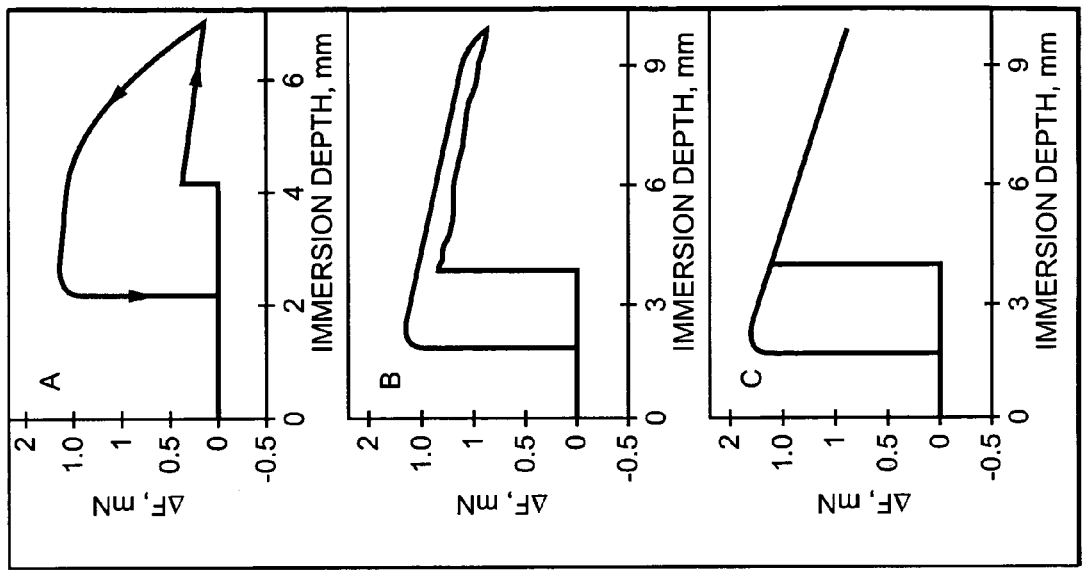
FIG. 2 is a graph showing hysteresis measurements of various surfaces.

The hysteresis-diagrams shown in FIG. 2 provide proof of the successful oxidation treatment. The test of the different surfaces of the titanium flakes took place here by way of the Wilhelmy Plate Method. The values for the single plates A, B and C are as follows:

A. Not Cleaned: $\theta_{vor}$=76.2°, $\theta_{Rück}$=18.2°, hysteresis: large
B. cleaned: $\theta_{Vor}$=36.5°, $\theta_{Rück}$=21.1°, hysteresis: small
C. Oxidized: $\theta_{Vor}$=20.0°, $\theta_{Rück}$=15.0°, hysteresis: none (Translator Note: The German subscripts "Vor" and "Rück" indicate forward and backward directions, respectively)

The advance angle (θVor) and the hysteresis are crucial. One can see that the flake (A) which was not cleaned, with an advance angle (θVor) of 76°, is very hydrophobic. The large hysteresis surface is an indication of impurities. The cleaned polished flakes (B) show improved characteristics with a significantly smaller contact angle of 36.5° and a marked decrease in the hysteresis. The best results were however achieved with the oxidized flakes (C), which have a contact angle of only 20° without visible hysteresis, in other words a thermodynamically unified surface.

EXAMPLE 11

Covalent Protein Coating of Titanium Flakes a) Hydroxylation with Nitric Acid

For the purposes of comparison, oxidized and nonoxidized titanium flakes were heated under reflux for 2 h at 80° C. in 5% HNO3. Afterwards the flakes were washed with 500 ml water (pH=6-7). The flakes were further washed with 30 ml dry ethanol.

b) Silanization

The nonoxidized or (as described above) oxidized titanium flakes were placed in heated containers for the silanization reaction. The containers should cool down in advance in a dry environment, preferably under nitrogen in a dessicator. 50 ml dry toluene and 2.5 ml APS are mixed under inert gas in an atmosbag (nitrogen). The container is loaded with the flakes as quickly as possible in air and is placed under inert gas in the round bottom flask with the APS/toluene mixture. It is closed and heated for 3 h under reflex. (Contact thermometer 140° C.) The flakes are rinsed three times with 10 ml trichloromethane, acetone and methanol. The flakes are dried in air.

c) Activation with Carbonyldiimidazole

After this the flakes in the container are placed in a solution of acetone (dried) and carbonyldiimidazole. The solution contains 50 ml acetone and 2.5 g CDI. The round bottom flask is closed under inert gas and is stirred for 4 h at room temperature. After this the flakes are rinsed three times with 10 ml acetone and water. The flakes are dried in air.

d1) Coating of Protein with 125I-Ubiquitin

After this the flakes are added individually to a buffer solution of 50 mM Na-phosphate buffer pH 10 containing a concentration of 1 mg/ml 125I-ubiquitin of a specific radioactivity of 5000-20000 cpm/μg. (The ubiquitin concentration can be between 0.01-1.0 mg/ml with or without 0.066% SDS.) The flakes are shaken for 12-14 h at room temperature. After this the flakes are washed four times each in phosphate buffer, a solution of 1.0 M NaOH, 1% sodium dodecyl sulfate (SDS) at room temperature and are then incubated 15 min at 60° in a solution of 0.1 M NaOH, 1% sodium dodecyl sulfate. Thorough washing with water follows (see Table 2 and FIGS. 3-4).

d2) Protein Coating with 125I-BMP-2

BMP-2 is radioactively labeled (specific radioactivity 5000-20000 cpm/μg) using the known Bolton-Hunter Method in a buffer of 125 mM sodium borate, 0.066% SDS, pH 8.4. The coupling of 125I-BMP-2 takes place in a buffer with 50 mM sodium borate, 0.066% SDS at pH 10. The concentration of 125I-BMP-2 can be between 0.01-1.0 mg/ml. The flakes are shaken for 12-14 h at room temperature. After this the flakes are washed four times each in phosphate buffer, a solution of 0.1 M NaOH, 1 sodium dodecyl sulfate (SDS) at room temperature and are then incubated 15 min at 60° in a solution of 0.1 M NaOH, 1% sodium dodecyl sulfate. Thorough washing with water follows.

TABLE 2

Protein coupling to titanium flakes by way of example of the protein 125I-ubiquitin

| | Immobilization of 125I-ubiquitin | | |
|---|---|---|---|
| | polished titanium flakes | with titanium flakes coated with oxide μg/cm2 | |
| | μg/cm2 | A | B |
| Adsorption experiment | | | |
| APS-flakes | 0.800 | 1.06 | 0.914 |
| Covalent coupling experiment | | | |
| "irreversible" nonspecific Adsorption (control) | 0.040 | 0.177 | 0.114 |
| App. covalent | 0.114 | 0.500 | 0.604 |
| Coupling | 0.106 | 0.446 | 0.589 |

TABLE 3

Comparative coupling of the proteins 125I-ubiquitin and 125I-BMP-2 to oxidized titanium flakes (treated with chromic-sulfuric acid, density 1.84) in the presence of 0.066% SDS

| Covalent coupling experiment | Immobilization of 125I-ubiquitin Oxide-coated titanium flakes μg/cm² |
|---|---|
| A. "Irreversable" nonspecific Adsorption (control) | |
| 125I-ubiquitin (0.01 mg/ml) | 0.003 |
| 125I-BMP-2 (0.01 mg/ml) | 0.005 |
| 125I-ubiquitin (1.0 mg/ml) | 0.172 |
| 125I-BMP-2 (1.0 mg/ml) | 0.1-0.2* |
| B. Covalent | |
| 125I-ubiquitin (0.01 mg/ml) | 0.009 |
| 125I-BMP-2 (0.01 mg/ml) | 0.010 |
| 125I-ubiquitin (1.0 mg/ml) | 0.570 |
| 125I-BMP-2 (1.0 mg/ml) | 0.4-0.6* |

*approximated

All derivatives of titanium flakes depicted in Table 2 have been tested in cell culture with osteoblasts descendants (MC3T3). Confluent cell lawns stimulable by BMP-2 formed on all flakes. The oxidized flakes yielded approximately twice as high stimulation rates. The results allow the conclusion that the flakes do not exhibit any toxicity, whereby the oxidized flakes were clearly better then the nonoxidized flakes.

Figure 3:
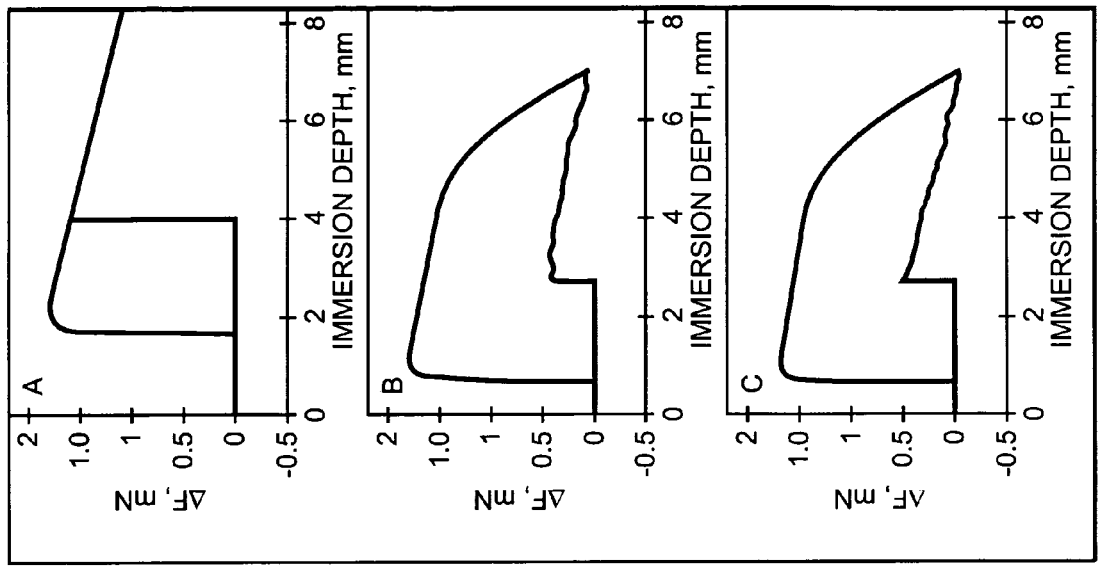
FIG. 3 is a graph showing the change in contact angle and hysteresis with non-oxidized titanium flakes following APS-modification and protein coupling.

FIG. 3 shows the change in contact angle and in hysteresis with nonoxidized (polished) titanium flakes following APS-modification and protein coupling. One can qualitatively monitor the coating, however no quantitative conclusions can be drawn. The values for the individual flakes A, B and C are as follows:

A. Cleaned $\theta_{Vor}$=36.5°, $\theta_{Rück}$=21.1°, hysteresis: small

B. APS-modified $\theta_{Vor}$=68.6°, $\theta_{Rück}$=22.6°, hysteresis: large

C. 125I-ubiquitin $\theta_{Vor}$=46.1°, $\theta_{Rück}$=17.41°, hysteresis: none (Translator Note: The German subscripts "Vor" and "Rück" indicate forward and backward directions, respectively)

Figure 4:
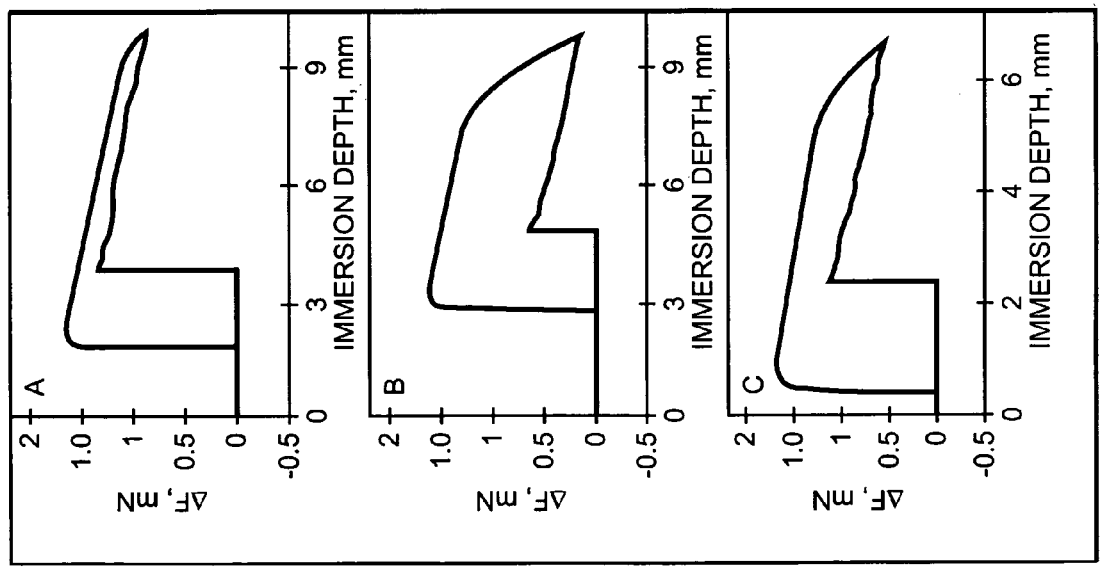
FIG. 4 is a graph showing the change in contact angle and hysteresis with oxidized titanium flakes following APS-modification and protein coupling.

FIG. 4 shows changes in contact angle and hysteresis with oxidized titanium flakes following APS-modification and protein coupling. One can similarly monitor the coating qualitatively here, however, no quantitative conclusions can be drawn. The values for the individual flakes A, B and C are as follows:

A. Cleaned $\theta_{Vor}$=36.5°, $\theta_{Rück}$=21.1°, hysteresis: small
B. APS-modified $\theta_{Vor}$=76.7°, $\theta_{Rück}$=15.9°, hysteresis: large
C. 125I-ubiquitin $\theta_{Vor}$=76.9°, $\theta_{Rück}$=48.2°, hysteresis: large (Translator Note: The German subscripts "Vor" and "Rück" indicate forward and backward directions, respectively)

EXAMPLE 12

Coating of Titanium Flakes with Agarose to Reduce Nonspecific Protein Adsorption (=Protein-Repellent Layer)

a) Oxidation of the Agorose with Sodium Periodate to Dialdehyde-Agorose

The reduction batch of 19 g 4% agarose-gel spheres (diameter: 40-190 µm) for example sepharose 4B, Pharmacia, 100 ml distilled water, 2.5 ml 0.4 M sodium periodate solution was treated as follows:

The agarose-gel spheres are first washed in a Büchner funnel with distilled water and are then shortly sucked dry by vacuum filtration. The moist gel cake is then taken up in 100 ml water. After addition of 2.5 ml 0.4 M sodium periodate, the agorose-gel suspension is stirred fo 4 h in the dark in an ice bath and then overnight at room temperature. After this the product is washed with distilled water, 3% sodium thiosulfate solution and again with distilled water, and water is finally removed with acetone. The finished agarose is subsequently dried under oil-pump vacuum at 30° C. Like the native agarose, the dialdehyde-agarose still has the ability to gel. Under these conditions, 1% of all agarobiose units are oxidized.

b) Coupling of dialdehyde-agarose to aminopropylsilyl Titanium Flakes

Reaction batch per flake:
4 ml of a solution of dry dialdehyde-agarose in potassium-phosphate buffer (0.1 M; pH=7.0) at 80° C.
Reaction batch a): 0.7% solution
Reaction batch b): 1.4% solution
Reaction batch c): 2.1% solution
Reaction batch d): 4.0% solution The dry dialdehyde-agarose is first dissolved in the buffer in the desired concentration (0.7-4%) at 80° C. The aminopropylsilyl titanium flakes (for production see above) are then placed in the solution in a holder, and stirring for 2 h at 80° C. follows. After 20 minutes 400 mg of sodium cyanoborohydride are added to reduce the Schiff bases formed. The product is finally washed with 15 ml each of 4M sodium chloride solution and water at 80° C. and finally with water at room temperature to remove excess agarose. Water is removed from the flakes with acetone, and these are then dried overnight at 30° C. under vacuum. The agarose layer on the titanium flakes can finally be activated as described with carbonyldiimidazole to couple primary amines (for example to aminoacids or proteins).

c) Activation of the agarose layer with carbonyldiimidazole 150 mg carbonyldiimidazole are dissolved in 3 ml acetone and are then added to the agarose-coated titanium flake. The flake is incubated for 2 h at room temperature and is then thoroghly rinsed with acetone and distilled water.

d1) Protein coating with 125I-Ubiquitin

After this the agarose flakes are added individually to a buffer solution of 50 mM sodium phosphate buffer pH 10 containing a concentration of 1 mg/ml 125I-ubiquitin with the specific radioactivity of 5000-20000 cpm/µg. (The ubiquitin concentration can be between 0.01 and 1.0 mg/ml.) The flakes are shaken for 12-14 h at room temperature. The reaction of the flakes by incubation with 40 mg/ml glycin in 50 mM sodium phosphate buffer pH 10 at room temperature is then timed for 4 h. Washing with 15 ml each of water, 1 M sodium chloride and water follows. Washing with 1 SDS at room temperature is also possible if required.

d2) Protein Coating with 125I-BMP-2

Figure 5:
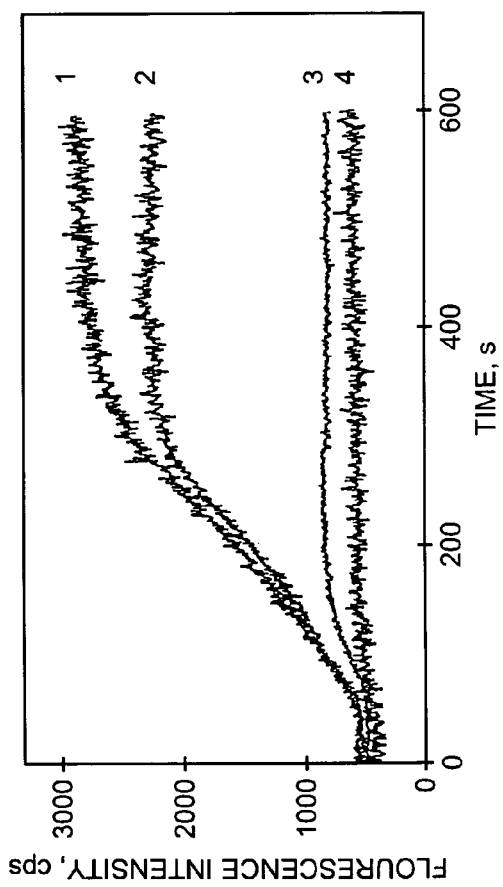
FIG. 5 is a graph showing the reduction of non-specific adsorption of fibrinogen by agarose coating of quartz glass plates.

BMP-2 is radioactively labeled (specific radioactivity of 5000-20000 cpm/µg) using the known Bolton-Hunter Method in a 125 mM sodium borate buffer. The coupling of 125I-BMP-2 takes place in a buffer with 50 mM sodium borate, 0.066% SDS at pH 10. The concentration of 125I-BMP-2 can be between 0.01-1.0 mg/ml. The flakes are shaken 12-14 h at room temperature. The reaction of the flakes by incubation with 40 mg/ml glycin in 50 mM sodium phosphate buffer pH 10 at room temperature is then timed for 4 h. Washing follows with 15 ml each of water, 1 M sodium chloride and water. Washing with 1% SDS at room temperature is also possible if required.

d3) Derivatization of quartz glass plates:

In an analogous method quartz glass plates can also be coated with agarose. The protein repellent effect (fibrinogen-adsorption, TIRF—(Total Inner Reflection Spectroscopy) method) can be especially well visualized on these flakes. FIG. 5 shows the reduction of the nonspecific adsorption of fibrinogen by agarose coating of quartz glass plates measured independent of time in the TIRF-Online-Method. The adsorption of fibrinogen (concentration 0.01 mg/ml) was carried out in 50 mM tris/HCl, 150 mM NaCl, 0.1 mM EDTA, pH 7.4. The fluoressence of tryptophan was excited at 290 nm and the emission was measured at 350 nm with a fluoressence spectrophotometer (Spex Fluorolog 112XI) under TIRF-conditions. The agarose was covalently bound in monomeric form to the amino function of the aminopropylsilyl moiety. cps: counted photons per second. The curves here have the following meanings:

curve 1: aminopropylsilyl-modified quartz glass plate
curve 2: unmodified quartz glass plate (control)
curve 3: quartz glass plate covalently coated with 0.7% agarose
curve 4: quartz glass plate covalently coated with 4% agarose

EXAMPLE 13

Protein Coating of Porous Hydroxylapatite (a Material for Replace the Bone)

a) Preparation of the hydroxylapatite
The following materials were used:
a. Porous hydroxylapatite (isolated from bovine bone) for example endobon, Merck, density: 1.289 g/cm³
b. 125I-Ubiquitin or 125I-BMP-2

3 ml dry toluene were mixed under nitrogen with 0.15 ml aminopropyl silane (APS). The porous hydroxylapatite (150 mg) is added and is boiled for 5 h under reflux. After this the hydroxylapatite is rinsed three times with acetone, three times with chloroform and three times with methanol. The porous hydroxylapatite is then poured into a solution of dry acetone (3 ml) and 150 mg of carbonyldiimidazole under nitrogen and is stirred for 3 h at room temperature. Rinsing three times with 10 ml acetone follows.

b1) Coupling of Protein with 125I-Ubiquitin

The hydroxylapatite from a) is transferred in 1 ml phosphate buffer (50 mM) pH 10.20 µl of ubiquitin (approximately: 50 mg/ml) and 10 µl radioactive ubiquitin (specific radioactivity of the final solution: 32600 cps/µg) are added to the phosphate buffer. The solution is mixed and is first rotation-stirred (German: am Rad gerührt) for 2 h at room temperature. Further stirring for 24 h at 4° C. follows. After this the modified hydroxylapatite is rinsed three times with water, and then four times with a solution of 0.1 M NaOH, 1% sodium dodecyl sulfate (SDS) and then three times with water. The radioactivity is measured in a gamma counter and the degree of substitution is determined. Controls with washed hydroxylapatite and/or with hydroxylapatite coated with APS are carried out (see Table 3).

b2) Coupling of Proteins with 125I-BMP-2

The hydroxylapatite from a) is transferred in 1 ml 50 mM Na-borate buffer, 0.066% SDS, pH 10. The coupling of 125I-BMP-2 (specific radioactivity see above) takes place in the same buffer (50 mM sodium borate, 0.066% SDS at pH 10) with incubation for 2 h at room temperature. Further stirring for 24 h at 4° C. follows. After this the modified hydroxylapatite is rinsed three times with water, then four times with a solution of 0.1 M NaOH, 1% sodium dodecyl sulfate (SDS) and then three times with water. The radioactivity is measured in a gamma counter and the degree of substitution is determined. Controls are carried out with washed hydroxylapatite and/or hydroxylapatite coated with APS. The concentration of 125I-BMP-2 in the coupling can be between 0.01-1.0 mg/ml.

TABLE 4

Coupling of protein to porous hydroxylapatite by way of example of the protein 125I-ubiquitin

| | Porous hydroxylapatite coupled ubiquitin µg/g |
|---|---|
| Control | 6 |
| 125I-ubiquitin | 24 |
| | 30 |

The invention claimed is:

1. A method of immobilization of a mediator molecule on an implant material, comprising:

covalently binding an anchor molecule to a chemically activated surface of the implant material, wherein the anchor molecule has a functional group having sufficient reactivity to allow covalent binding of a chemical compound;

binding an agarose spacer molecule to the anchor molecule, wherein the agarose spacer molecule has an additional functional group having sufficient reactivity for covalent binding of the mediator molecule;

covalently immobilizing a mediator molecule on the implant material using the additional functional group;

wherein the mediator molecule comprises a biomolecule that at least one of (a) reduces rejection of the implant material, and (b) promotes growing-in of the implant material; and wherein said implant material comprises at least one component selected from the group consisting of a metal, a metallic alloy, and a ceramic material.

2. The method according to claim 1 wherein the anchor molecule comprises an aminoalkylsilane molecule.

3. The method according to claim 1 wherein the chemically activated surface of the implant material is provided with an oxide layer prior to covalent binding of the anchor molecule.

4. The method according to claim 1 wherein the biomolecule is BMP protein.

5. The method according to claim 4 wherein the BMP protein is BMP-2 or BMP-7.

6. The method according to claim 1 wherein the biomolecule is ubiquitin.

7. The method according to claim 1 wherein the biomolecule is an antibiotic.

8. An implant with a mediator molecule immobilized thereon produced by the method of claim 1.

9. The implant according to claim 8 wherein the metal of the implant material comprises titanium, aluminum, or stainless steel, wherein the metallic alloy of the implant material comprises titanium, and wherein the ceramic of the implant material comprises hydroxyapatite.

* * * * *